US005473699A

United States Patent [19]

Tamamura et al.

[11] Patent Number: 5,473,699

[45] Date of Patent: Dec. 5, 1995

[54] VEHICLE INTERNAL NOISE REDUCTION SYSTEM

[75] Inventors: Manpei Tamamura, Ohta; Hiroshi Iidaka, Koganei; Eiji Shibata, Gunma, all of Japan

[73] Assignee: Fuji Jukogyo Kabushiki Kaisha, Tokyo, Japan

[21] Appl. No.: 234,018

[22] Filed: Apr. 28, 1994

[30] Foreign Application Priority Data

May 21, 1993 [JP] Japan .................................... 5-120193

[51] Int. Cl.[6] ............................ A61F 11/06; H03B 29/00

[52] U.S. Cl. .............................. 381/71; 381/73.1; 381/94

[58] Field of Search ................................ 381/71, 86, 94, 381/73.1

[56] References Cited

U.S. PATENT DOCUMENTS 4,677,676 6/1987 Eriksson .................................... 381/71
5,172,416 12/1992 Allie et al. ................................ 381/71
5,295,192 3/1994 Hamada et al. .......................... 381/71

*Primary Examiner*—Curtis Kuntz
*Assistant Examiner*—Xu Mei
*Attorney, Agent, or Firm*—Beveridge, DeGrandi, Weilacher & Young

[57] ABSTRACT

A primary source is synthesized with a filter coefficient of a first adaptive filter into a canceling signal. The canceling signal is converted into a canceling sound and the canceling sound is generated from a speaker. A result of interference of the canceling sound with a noise sound is detected by a microphone as an error signal. The error signal is subjected to a sum of convolution products with the filter coefficient of the first adaptive filter in a LMS calculation circuit and the filter coefficient is updated therein. On the other hand, the error signal is subjected to a sum of convolution products with the canceling signal in another LMS calculation circuit and a filter coefficient of a second adaptive filter is updated. The updated filter coefficient of the second adaptive filter is sent to a compensation coefficient synthesizing circuit and therein the compensation coefficient is corrected by the filter coefficient. The corrected compensation coefficient updates the filter coefficient of the first adaptive filter. As a result, the first adaptive filter is automatically adjusted so as to reflect actual transmission characteristics in the passenger compartment, whereby a noise reduction with a stable performance is always obtained under any conditions of the passenger compartment.

8 Claims, 4 Drawing Sheets

VEHICLE INTERNAL NOISE REDUCTION SYSTEM

BACKGROUND OF THE INVENTION

The present invention relates to a noise reduction system for a passenger compartment of an automotive vehicle by positively generating a sound from a sound source to cancel the vehicle internal noise.

There have been proposed several techniques for reducing the noise sound in the passenger compartment by producing a canceling sound, having the same amplitude as the noise sound and a reversed phase thereto, from a sound source disposed in the passenger compartment.

In a recent example, Japanese application laid open No. 1991-178845 disc loses a vehicle internal noise reduction technique for reducing a noise sound by using a LMS (Least Means Square) algorithm (a theory for obtaining a filter coefficient by approximating it to an instanteneous means square error in order to simplify a formula, utilizing that a filter correction formula is a recursive expression or by employing a MEFX-LMS (Multiple Error Filtered X-LMS) algorithm. This technique has already been put to a practical use in some of production vehicles.

Commonly, an internal noise reduction system using this LMS algorithm is composed such a way that: a vibration noise source signal (primary source) is detected from an engine, then the primary source is synthesized with a filter coefficient of an adaptive filter into a canceling sound, then the canceling sound is generated from a speaker to cancel a noise sound in the passenger compartment, further the noise sound reduced by the canceling sound is detected as an error signal by a microphone disposed at a noise receiving point, and based on the detected error signal and a primary source signal synthesized with a compensation coefficient (a coefficient mainly representing a speaker/microphone transmission characteristic as a finite impulse response), a filter coefficient of the adaptive filter is updated by the LMS algorithm so as to optimize the reduced noise sound at the noise receiving point.

However, in the above mentioned internal noise reduction system utilizing a LMS algorithm or a MEFX-LMS algorithm, there is a problem that the compensation coefficient representing a speaker/microphone characteristic deviates substantially from a desired value when the speaker/microphone characteristic varies due to changes of miscellaneous conditions within the passenger compartment, such as a change of the number of passengers, a change of temperature in the passenger compartment and a deterioration of the speaker performances, and consequently a deviation of time, namely a deviation of phase is caused and a result it becomes difficult to reduce a noise because of the erroneous positioning where an adaptive filter is to be updated.

SUMMARY OF THE INVENTION

The present invention has been made in order to overcome the aforementioned problem. An object of the present invention is to provide an internal noise reduction system for a vehicle that can constantly and effectively reduce a noise sound within the passenger compartment by compensating a deviation between a compensation coefficient and an actual speaker/microphone characteristic even when there occur some changes in the conditions of the passenger compartment, such as the number of passengers, temperature in the passenger compartment or the performance of the speaker.

To achieve the above object, the internal noise reduction system according to the present invention comprises:

first canceling signal synthesizing means for synthesizing the primary source signal with a first filter coefficent of a first adaptive filter and for producing a canceling signal; canceling sound generating means responsive to the canceling signal for generating a canceling sound from a sound source so as to cancel a noise sound within said passenger compartment; error signal detecting means for detecting a state of noise reduction at a noise receiving point as an error signal; compensation coefficients synthesizing means for synthesizing the primary source signal with a compensation coefficient and for outputting an output signal; first filter correction amount calculating means responsive to the output signal from the compensation coefficients synthesizing means and to the error signal from the error signal detecting means for calculating a first correction amount and outputting said first correction amount signal; first filter coefficients updating means for correcting the first filter coefficient based upon the first correction amount signal and for sending the corrected first filter coefficient to the first canceling signal synthesizing means; second canceling signal synthesizing means for synthesizing the canceling signal with a second filter coefficient of a second adaptive filter and for outputting a synthesized canceling signal; error signal adding means for adding the synthesized canceling signal and the error signal and for outputting a product of the addition as an addition signal; second filter correction amount calculating means responsive to the canceling signal from the first canceling signal synthesizing means and the addition signal from the error signal adding means for calculating a second correction amount and outputting a second correction amount signal; second filter coefficients updating means for updating the second filter coefficient based upon the second correction amount signal and for producing the updated second filter coefficient so as to cancel a deviation of a transmission characteristic between the canceling sound generating means and the error signal detecting means; correction control means responsive to the addition signal, the error signal and the primary source signal for generating a correction control signal; and compensation coefficients correcting means responsive to the correction control signal for correcting the compensation coefficient from the second filter coefficients updating means and for sending the compensation coefficient involving an effect of an actual transmission characteristic between the canceling sound generating means and the error signal detecting means to the compensation coefficients synthesizing means.

Next, based on the composition of means abovementioned, a brief description about a function of the noise reduction system according to the present invention will be made.

First, when a noise sound whose primary source is an engine vibration noise is generated in the passenger compartment, in the canceling signal synthesizing means a vibration noise source signal having a high correlation with an engine vibration noise is synthesized into a canceling signal by a first adaptive filter, then in the canceling sound generating means the canceling signal is transformed into a canceling sound, then the canceling sound is generated to cancel the noise sound in the passenger compartment. Next, in the error signal detecting means the state of noise reduction is detected as an error signal, then the error signal is transmitted to the first filter correction amount calculating means. Further, the vibration noise source signal is synthesized with a compensation coefficient by the compensation coefficients synthesizing means and the synthesized vibration noise is outputted to the first filter correction amount calculating means. Then, in the first filter correction amount calculating means, based upon an output signal from the compensation coefficients synthesizing means and the error signal a correction amount of the first filter coefficient of the first adaptive filter is obtained. Then in the first filter coefficients updating means the first filter coefficient is updated by the correction amount of the first filter coefficient.

On the other hand, the canceling signal from the first canceling signal synthesizing means is inputted to the second canceling signal synthesizing means in which the canceling signal is synthesized with the second filter coefficient of the second adaptive filter, then in the error signal adding means the synthesized canceling signal is added by the error signal, then based upon the addition signal and the canceling signal the correction amount of the second filter coefficient is calculated in the second filter correction amount calculating means, then in the second filter coefficients updating means the second filter coefficient is updated by the correction amount of the second filter coefficient.

Further, in the correction control means, based on the addition signal, the error signal and the vibration noise source signal (primary source signal), the correction control signal is generated if the required conditions are met. When the correction control signal is generated, the compensation coefficient is corrected by the second filter coefficient signal from the second filter coefficients updating means.

BRIEF DESCRIPTION OF THE DRAWINGS

The present invention will be described hereinafter in connection with the accompanying drawings, in which:

FIG. 1 is a schematic diagram representing a vehicle internal noise reduction system and FIG. 2 is a block diagram representing an ignition signal conversion circuit. FIG. 3 is a flow diagram representing steps for correcting a compensation coefficient.

DETAILED DESCRIPTION OF THE PREFERRED EMBODIMENT

Figure 1:
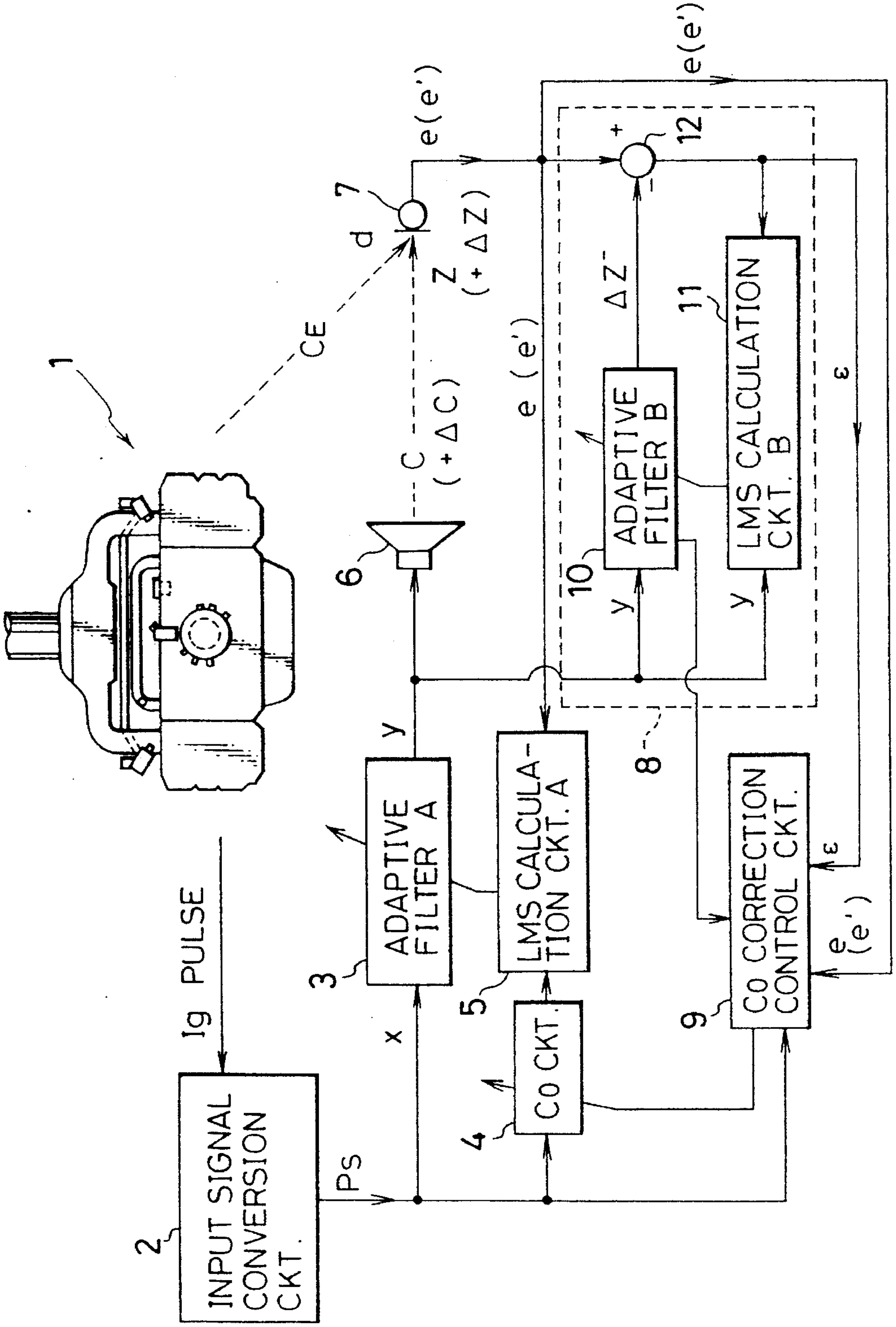
FIG. 1 to FIG. 3 represents an embodiment of the present invention, among them
Figure 2:
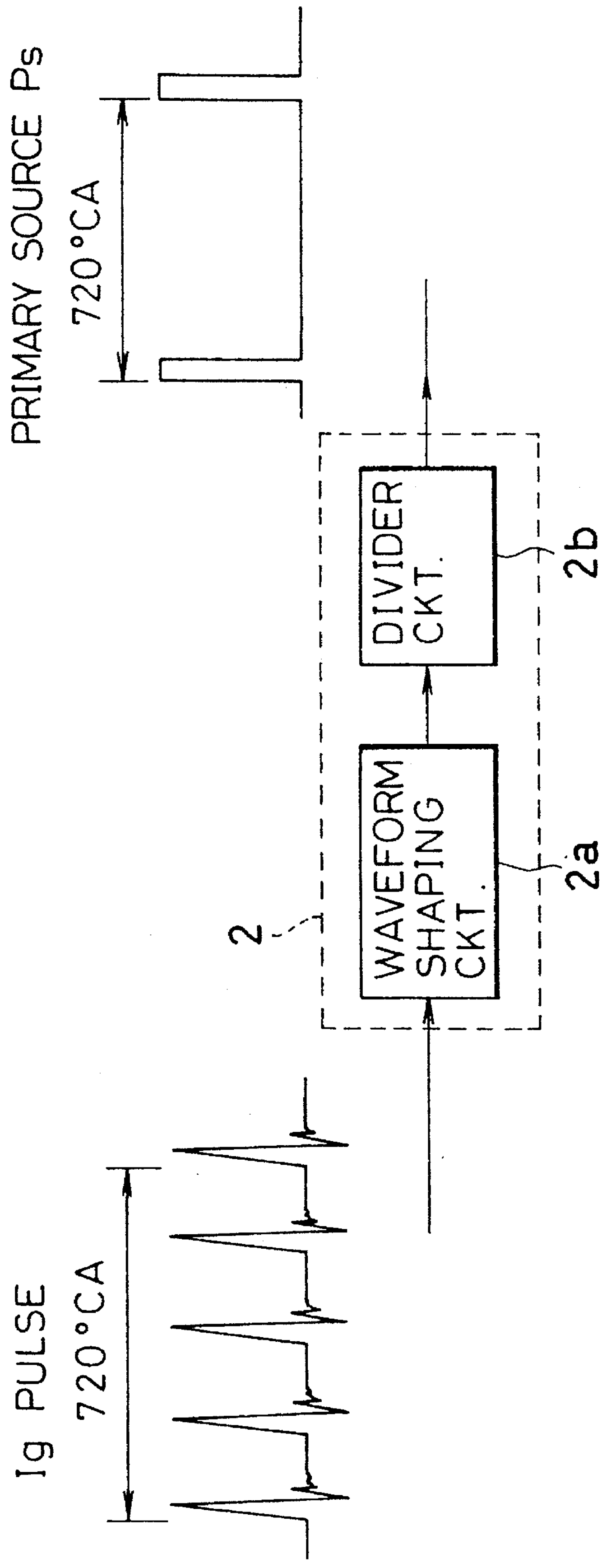

Referring to FIG. 1, numeral 1 denotes a four strokes engine from which an ignition pulse signal $I_g$ is outputted not only to an ignition coil (not shown) but also to an input signal conversion circuit 2. The input signal conversion circuit 2 is composed of a waveform shaping circuit 2*a* and a frequency divider circuit 2*b*, as depicted in FIG. 2. The ignition pulse signal $I_g$ inputted to the input signal conversion circuit 2 is shaped and divided into a signal composed of one pulse per two engine revolutions including frequencies of 0.5 ×n (n: integers) order and is outputted as a vibration noise source signal (primary source $P_s$) to a first adaptive filter (hereinafter, referred to as an adaptive filter A) forming a first canceling signal synthesizing means, a speaker/microphone transmission characteristics correcting circuit (hereinafter, referred to as a $C_0$ circuit) 4 forming a compensation coefficients correcting means and a compensation coefficients synthesizing means, and a $C_0$ correction control section 9 forming a correction control means, The noise sound derived from the four strokes engine is a noise sound forming one cycle per two engine revolutions because the engine 1 has four strokes (induction, compression, explosion and exhaust) per two engine revolutions, i.e., 720 degrees of crank angle. According to a frequency analysis, the noise frequency spectrum is mainly composed of 0.5 order component per two engine revolutions (one-cycle sine wave component for every two engine revolutions) as a fundamental harmonic wave and higher order components of 0.5 ×n (integers). Accordingly, by means of processing the ignition pulse Ig in the manner as described before, a primary source Ps having a very high correlation with a noise sound to be reduced is obtained.

The abaptive filter A 3 is a FIR (Finite Impulse Response) filter which has a filter coefficient $W_{A(n)}$ being able to be corrected by a LMS calculation circuit A 5 as a first filter correction amount calculating means. Further, the adaptive filter A 3 is provided with a specified number of taps. The primary source $P_s$ (referred to as an input signal x, hereinafter) inputted to the adaptive filter A 3 is subjected to the sum of convolution products process with the filter coefficient $W_{A(n)}$ and outputted as a canceling signal (referred to as an output signal y, hereinafter) to a compensation coefficients correcting circuit 8 forming a second canceling signal synthesizing means, an error signal adding means, a second filter coefficients updating means and a second filter correction amount calculating means, and to a speaker 6 forming a canceling sound generating means via a D/A converter (not shown), a filter circuit (not shown) and an amplifier circuit (not shown). The output signal y outputted to the speaker 6 is transformed into a canceling sound therein and the canceling sound is generated from the speaker 6.

The speaker 6 is disposed at the inner side of the front door or the like in the passenger compartment and on the other hand an error microphone 7 forming an error signal detecting means is incorporated at the noise receiving point within the passenger compartment (for example, a position adjacent to ears of a driver).

An error signal e (a signal indicating an interference result of the canceling sound and the engine related noise sound and it is expressed as e=d+Z, where d is a noise sound detected by the error microphone 7 and Z is a canceling sound detected by the error microphone 7) is inputted to the LMS calculation circuit A, the compensation coefficients correcting circuit 8 and the $C_0$ correction control section 9 via an amplifier circuit (not shown), a filter circuit (not shown) and an A/D converter (not shown).

Further, in the $C_0$ circuit 4, a speaker/microphone transmission characteristic C is stored as a value approximated to a finite impulse response. The speaker/microphone transmission characteristic C is a reference value which has been determined beforehand under a cetain standard condition of the passenger compartment. Actually, this reference value becomes a compensation coefficient $C_0$ after being subjected to a correction by the $C_0$ correction control section 9.

The input signal x is multiplied (sum of convolution products) by the corrected compensation coefficient $C_0$ and then outputted to the LMS calculation circuit A 5.

Further, this LMS calculation circuit A 5 is a circuit in which, based upon the error signal detected by the error microphone 7 and the primary source $P_s$ corrected in the $C_0$ circuit 4, a correction amount of the filter coefficient $W_{A(n)}$ for the adaptive filter A 3 is obtained by a well known LMS algorithm and the filter coefficient $W_{A(n)}$ is updated accordingly.

On the other hand, the compensation coefficient correcting circuit 8 to which an output signal y and an error signal e are inputted comprises a second adaptive filter (referred to as an adaptive filter B, hereinafter) 10, a LMS calculation circuit B 11 for updating a filter coefficient $W_{B(n)}$ of the adaptive filter B 10, and an addition circuit 12. The circuit is so constituted that the output signal y is inputted to the adaptive filter B 10 and the LMS calculation circuit 11 and the error signal e is inputted to the addition circuit 12.

The circuit is so constituted that the output signal y inputted to the adaptive filter B 10 is subjected to the sum of convolution product process with the filter coefficient $W_{B(n)}$ of the adaptive filter B 10 and outputted to the addition circuit 12 as a signal ΔZ'. In this addition circuit 12 the circuit is so constituted that the signal ΔZ' is added by the error signal e and the added signal $\epsilon(\epsilon=e+\Delta Z')$ is inputted to the LMS calculation circuit B 11 and the $C_0$ correction control section 9.

The adoptive filter B 10 is, like the adaptive filter A 3, a FIR filter which has a filter coefficient $W_{B(n)}$ being able to be updated by the LMS calculation circuit B 11. Further, the adaptive filter B 10 is provided with a specified number of taps. The LMS calculation circuit B 11 is a circuit in which, based upon the input signal y and the added signal ε, a correction amount of the filter coefficient $W_{B(n)}$ for the adaptive filter B 10 is obtained by means of a well known LMS algorithm and the filter coefficient $W_{B(n)}$ is updated. Further, on the other hand the filter coefficient $W_{B(n)}$ of the adaptive filter B 10 is outputted also to the $C_O$ correction control section 9.

Further, the $C_0$ correction control section 9 is connected to the $C_0$ circuit 4. The circuit is so constituted that the updated filter coefficient $W_{B(n)}$ is transmitted to the $C_0$ correction control section 9 where the compensation coefficient $C_0$ can be corrected according to the process as will be described hereinafter.

The signals e and ε inputted to the $C_0$ correction control section 9 are memorized therein for some consecutive time and based on these memorized signals, mean scquare values E [e2] and E [ε2] are calculated and stored in the $C_O$correction control section 9.

Further, the $C_0$ correction control section 9 is so constituted that the primary source $P_s$ inputted thereto and based on the pulse interval of the primary source $P_s$ the present engine speed $N_{E(n)}$ and the previous engine speed $N_{E(n-1)}$ are calculated and stored therein.

In Fig. 1 symbol ΔC indicates a deviation value of the speaker/microphone transmission characteristic, symbol ΔZ indicates a deviation value of the canceling signal detected by the error microphone 7, symbol e' shows an after-changed value of the signal detected by the error microphone 7 (e'=d+Z+ΔZ), and symbol $C_E$ shows a body transmission characteristic with respect to the vibration noise of the engine 1.

Figure 3:
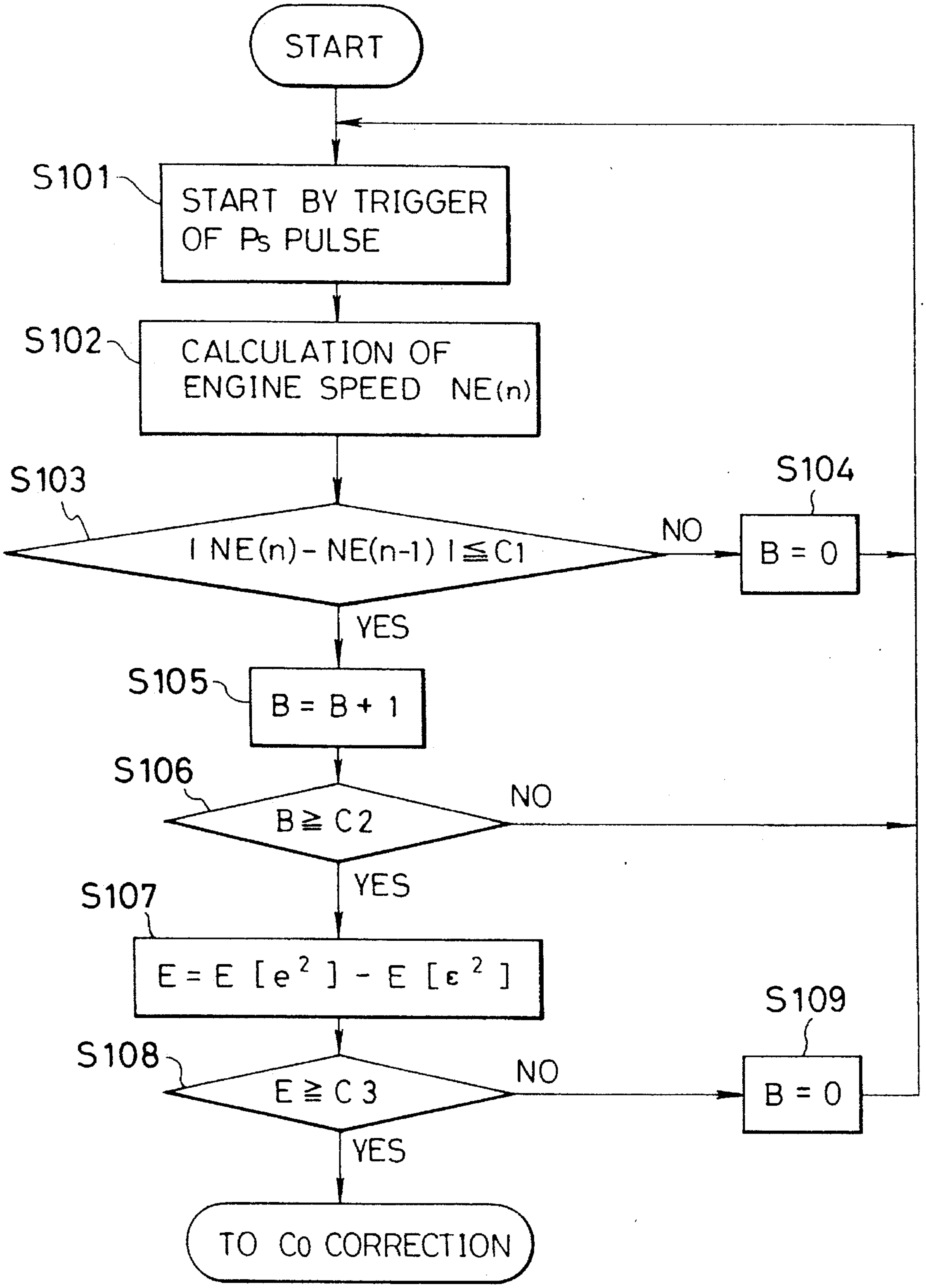
Figure 4:
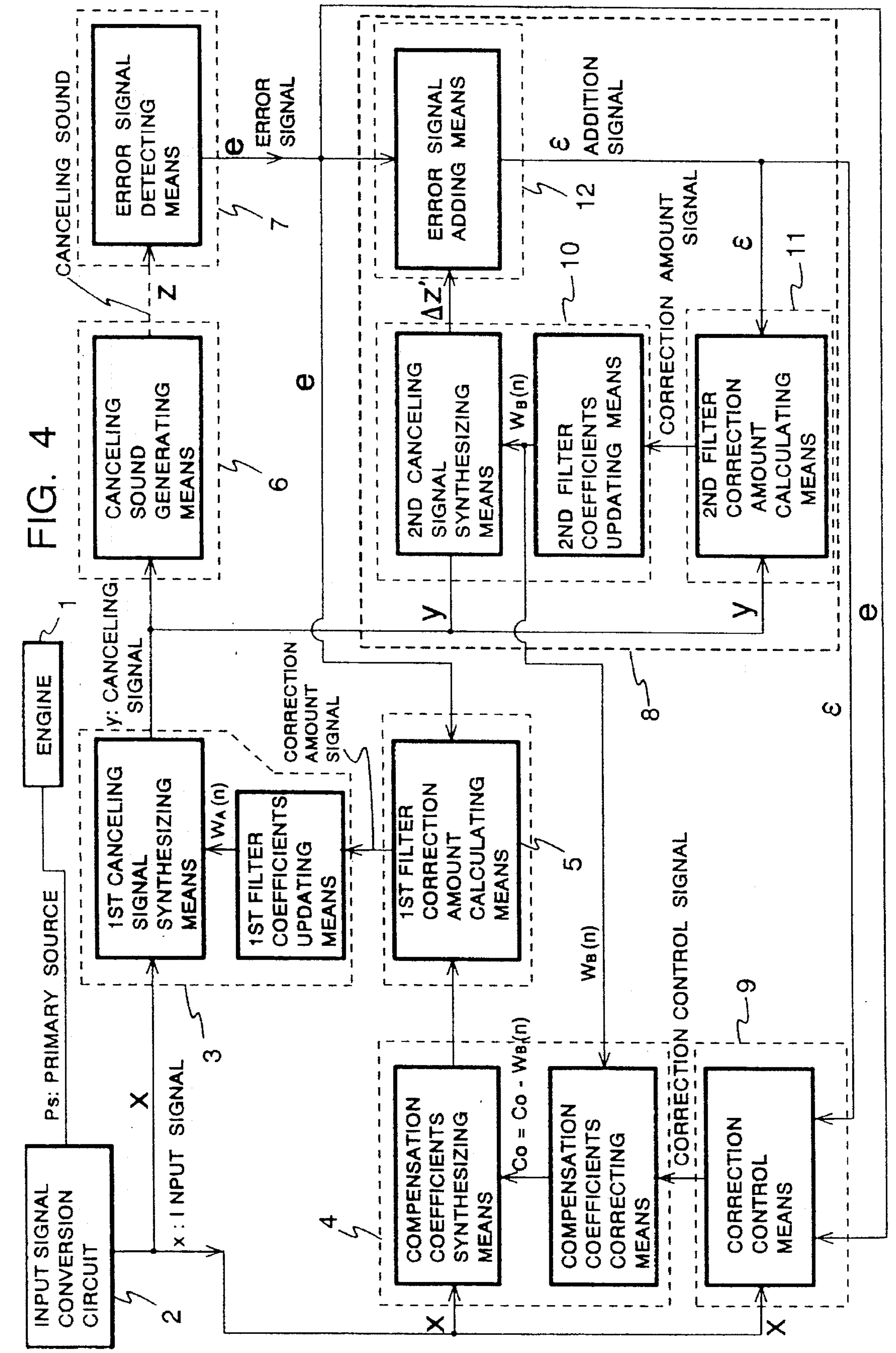
FIG. 4 is a block diagram showing means comprising the embodiment of the present invention.

Next, the $C_0$ correction process executed in the $C_0$ correction control section 9 will be described according the flowdiagram shown in FIG. 3.

When a power source is switched on, the flow is started to be carried out. First, at a step (hereinafter, referred to as "S") 101, the process is started on a triggering of an inputted pulse of the primary source $P_s$ and it goes to S102 where the present engine speed $N_{E(n)}$ is calculated based upon the pulse interval of the primary source $P_s$.

Next, the process goes to S103 where an absolute value of the difference of the present engine speed $N_{E(n)}$ and past engine speed $N_{E(n-1)}$ is calculated. If the absolute value is larger than a predetermined value C1 ($|N_{E(n)}-N_{E(n-1)}|>C1$), the process steps to S104 at which a counter B is set to be 0 (B=0) and then returns to S101. If $|N_{E(n)}-N_{E(n-1)}|\leqq C1$, it is judged that the engine operation normal condition and the process goes to S105.

When the process goes to S105, the counter B is counted up (B=B+1) therein and the process steps to S106 where it is judged whether or not the counter B is larger than C2. If the counter B is smaller than C2, then the process returns to S101 again and if the counter B is equal to or larger than C2 (B≧C2), the process goes to S107 where, based upon the aforementioned mean square vales E $[e^2]$ and E $[\epsilon^2]$, the difference between these two values E (E=E $[e^2]$−E $[\epsilon^{2]}$) is calculated and the process goes to S108, At S108 it is judged whether or not this E is larger than a predetermined value C3. If E is smaller than C3 (E<C3), the process goes to S109 where the counter B is set to be 0 (B=0) and returns to S101 again. If E is equal to or larger than C3 (E≧C3), then the compensation coefficient $C_0$ in the $C_0$ circuit 4 is corrected as much as an amount corresponding to the deviation amount ΔC.

Since there is a step like S103, in such a case as the compensation coefficient $C_0$ is not changed but the error signal e is changed so much like when a vehicle is in acceleration or deceleration, the compensation coefficient is not corrected. Further, when the difference E of mean square values becomes larger than C3 at S107, it is designed such that the compensation coefficient $C_0$ is subjected to a correction, therefore, if the compensation coefficient $C_0$ represents the actual speaker/microphone transmission characteristic with some extent of fidelity, the compensation coefficient $C_0$ is not corrected.

Next, the function of the preferred embodiment according to the aforementioned compositions will be described.

First, an engine vibration noise is transfered from the engine 1 to the engine mountings (not shown) from which an internal noise sound is generated. On the other hand, the sound from an induction and exhaust system is also transfered into the passenger compartment. These engine related noise sounds are mainly composed of frequency spectrum of 0.5×n (n: integers) order component when expressed in a frequency domain and reach a noise receiving point (for example, a point adjacent to a driver's ears) after being subject to an effect of a body transmission characteristic $C_E$ corresponding to each noise source.

On the other hand, the ignition pulse signal $I_g$ from the engine 1 is inputted to the input signal conversion circuit and it is shaped and divided by the waveform shaping circuit **2*a* and the divider circuit 2*b* thereof into a signal of one pulse per two engine revolutions including a signal composed of 0.5×n (n; integers) order component when expressed in a frequency domain. The shaped and divided ignition pulse is outputted as a vibration noise source signal $P_s$ to the adaptive filter A 3, the speaker/micropone transmission characteristic correcting circuit (referred to as a $C_O$ circuit, hereinafter) 4 and the $C_0$ correction control section 9**.

First, a description will be made about the case where an actual speaker/microphone transmission characteristic C is in a standard state, namely the case where the compensation coefficient $C_0$ in the $C_0$ circuit represents the actual speaker/microphone transmission characteristic C with an approximate fidelity.

The primary source $P_s$ (input signal x) inputted to the adaptive filter A 3 is subjected to the sum of convolution products therein with the filter coefficient $W_{A(n)}$ of the adaptive filter A 3 and outputted as a canceling signal (output signal y) to the compensation coefficients correcting circuit 8 and the speaker 6 via the D/A converter (not shown), the filter circuit (not shown) and the amplifier circuit (not shown). The output signal y is outputted as a canceling sound to cancel a noise sound at the noise receiving point from the speaker 6. Then, the canceling sound reaches the noise receiving point after being subjected to an effect of the speaker/microphone transmission characteristic C.

At the noise receiving point, the canceling sound is interfered with the noise sound from the engine and reduces the noise sound and at the same time the result of interference is detected as an error signal e (e=d+Z) by the error microphone 7 disposed nearby the noise receiving point. The error signal e is inputted to the LMS calculation circuit A 5, the compensation coefficients correcting circuit 8 and the C0 correction control circuit 9 via the amplifier circuit (not shown), the filter circuit (not shown) and the A/D converter (not shown).

Further, the input signal x inputted to the $C_0$ circuit 4 is subjected to the sum of convolution products with an actual speaker/microphone transmission characteristic C which is approximated to a finite impulse response, namely a compensation coefficient $C_0$ and outputted to the LMS calculation circuit A 5, In the LMS calculation circuit A 5, based on the signal from the $C_0$ circuit and the error signal e, a correction value of the filter coefficient $W_{A(n)}$ is obtained according to a well known LMS algorithm and the filter coefficent $W_{A(n)}$ is updated.

Further, the signal y inputted to the compensation coefficients correcting circuit 8 is inputted to the adaptive filter B 10 of the compensation coefficients correcting circuit 8 and to the LMS calculation circuit B 11. Further, the error signal e from the error microphone 7 is inputted to the addition circuit 12 of the compensation coefficients correcting circuit 8.

In this case where the compensation coefficient $C_0$ represents an actual speaker/microphone transmission characteristic C faithfully, the signal e gradually converges to 0 (e=d+Z=0) by updatings of the filter coefficient $W_{A(n)}$ of the adaptive filter A 3.

Further, the signal y inputted to the adaptive filter B 10 is subjected to the sum of the convolution products with the filter coefficient $W_{B(n)}$ of the adaptive filter B 10 and then inputted as a signal ΔZ to the addition circuit 12 in which it is added by the signal e.

The addition signal $\epsilon(\epsilon=e+\Delta Z'=0+\Delta Z'=\Delta Z')$ is inputted to the LMS calculation circuit B 11 in which a correction amount of the filter coefficient $W_{B(n)}$ of the adaptive filter B 10 is obtained based upon the signal y and the addition signal e according to the well known LMS algolithm and thus the filter coefficient $W_{B\,(n)}$ is updated. That is to say, the filter coefficent $W_{B(n)}$ is updated so that the addition signal $\epsilon(\epsilon=\Delta Z')$ becomes 0.

Further, in the $C_0$ correction control section 9. a long time mean square value $E\,[e^2]$ and a long time mean square value $E\,[\epsilon^2]$ are calculated and monitored therein. Only when the difference between the $E\,[e^2]$ at the steady operating condition (judged from the pulse interval of the inputted signal x) and the $E\,[\epsilon^2]$ exceeds a specified value, it is arranged so as to correct the compensation coefficient $C_0$, accordingly in this case where the compensation coefficient $C_0$ represents an actual speaker/microphone transmission characteristic C faithfully, both $E\,[e^2]$ and $E\,[\epsilon^2]$ becomes almost 0 and therefore the correction of the compensation coefficient $C_0$ is not performed.

Next, the description will be made about the case where an actual speaker/microphone transmission characteristic C has been changed into C+ΔC (ΔC: variation), for example, because of an increase of the number of passengers or a temperature rise within the passenger compartment. Now, the abovementioned variation ΔC is assumed to be a variation causing not only a change of level but also a change of phase, because, if it is only a change of level, the problem can be solved by just updating the adaptive filter A 3 as described in the previous case.

The primary source $P_s$ (input signal x) inputted to the adaptive filter A 3 is subjected to the sum of convolution products therein with the filter coefficient $W_{A(n)}$ of the adaptive filter A 3 and outputted as a canceling signal (output signal y) to the compensation coefficients correcting circuit 8 and the speaker 6 via the D/A converter (not shown), the filter circuit (not shown) and the amplifier circuit (not shown). The output signal y is outputted as a canceling sound to cancel a noise sound at the noise receiving point from the speaker 6. Then, the canceling sound reaches the noise receiving point after being subjected to an effect of the speaker/microphone transmission characteristic C+ΔC.

At the noise receiving point, the canceling sound is interfered with by the noise sound from the engine and reduces the noise sound and at the same time the result of interference is detected as an error signal e' (e'=d+Z+ΔZ=e+εZ) by the error microphone 7 disposed nearby the noise receiving point. The error signal e' is inputted to the LMS calculation circuit A 5, the compensation coefficients correcting circuit 8 and the $C_0$ correction control circuit 9 via the amplifier circuit (not shown), the filter circuit (not shown) and the A/D converter (not shown).

Further, the input signal x inputted to the $C_0$ circuit 4 is subjected to the sum of convolution products with a compensation coefficient $C_0$ before change and outputted to the LMS calculation circuit A 5. In the LMS calculation circuit A 5, based on the signal from the $C_0$ circuit and the error signal e', a correction value of the filter coefficient $W_{A(n)}$ is obtained according to a well known LMS algorithm and the filter coefficent $W_{A(n)}$ is updated. It should be noted that it is impossible to compensate for the variation ΔC only by correcting the filter coefficient $W_{A(n)}$, since there is a deviation as much as an amount of ΔC between the compensation coefficent $C_0$ and the actual speaker/microphone transmission characteristic.

Further, the signal y inputted to the compensation coefficients correcting circuit 8 is inputted to the adaptive filter B 10 of the compensation coefficients correcting circuit 8 and to the LMS calculation circuit B 11. Further, the error signal e' from the error microphone 7 is inputted to the addition circuit 12 of the compensation coefficients correcting circuit 8. Further, the signal y inputted to the adaptive filter B 10 is subjected to the sum of the convolution products with the filter coefficient $W_{B(n)}$ of the adaptive filter B 10 and then inputted as a signal ΔZ' to the addition circuit 12 in which it is added by the signal e'. That is to say, the addition signal of the addition circuit 12 is:

$$\epsilon=e'+\Delta Z'=d+Z+\Delta Z+\Delta Z'=e+\Delta Z+\Delta Z'$$

However, since the error signal e before change converges to 0, ε is:

$$\epsilon=0+\Delta Z+\Delta Z'=\Delta Z+\Delta Z'$$

Further, the addition signal Δis inputted to the LMS calculation circuit B 11 where based upon the signal y and the addition signal e a correction amount of the filter coefficient $W_{B(n)}$ of the adaptive filter B 10 is obtained and thus the filter coefficient $W_{B(n)}$ is updated. That is to say, the filter coefficient $W_{B(n)}$ is updated so that the addition signal $\epsilon(=\Delta Z+\Delta Z')$ becomes 0 by setting $\Delta Z'=-\Delta Z$.

As a result of this, the filter coefficient $W_{B(n)}$ becomes a value representing a deviation $\Delta C$ of the actual speaker/microphone transmission characteristic C. Hereinafter, the compensation coefficient $C_0$ of the $C_0$ circuit 4 is corrected ($C_0=C_0-W_{B(n)}$) according to the correction process as described before.

Thus, according to the present embodiment, since a correction of the compensation coefficient $C_0$ in the internal noise reduction system is performed automatically, the vehicle internal noise reduction system according to the present invention makes a driver free from such a troublesome work as he must correct the compensation coefficient $C_0$ periodically.

Further, according to the present invention, since the compensation coefficient $C_0$ properly represents an actual speaker/microphone transmission characteristic, the best condition of noise reduction can always be obtained, even if actual speaker/microphone characteristics flucuate due to a change of the number of passengers, a change of temperature within the passenger compartment, a change of the system characteristics by aging or the like.

In this embodiment, an ignition pulse $I_g$ is employed as a primary source $P_s$, however other signal having a high correlation with an engine related vibration noise, such as a fuel injection pulse $T_i$, may be used as a primary source $P_s$.

Further, in this embodiment an example of the noise reduction system, in which a LMS algorithm of one channel (one microphone and one speaker) is employed, has been explained hereinbefore, however this noise reduction system can be applied to a noise reduction system using a MEFX-LMS (Multiple Error Filtered X-LMS) algorithm of multi-channels (for example, four microphones and four speakers).

In summary, the vehicle internal noise reduction system according to the present invention is characterized in that: in addition to synthesizing a canceling signal by a first adaptive filter and generating a canceling sound from a speaker, further synthesizing the canceling signal by a second adaptive filter and adding the synthesized canceling signal to an error signal which is a result of noise reduction, further, based upon this addition signal, the error signal and an engine vibration noise source signal, automatically correcting a compensation coefficient $C_0$ stored in a $C_0$ circuit so as to equalize to an actual speaker/microphone transmission characteristic C. Consequently, the noise reduction system according to the present invention can obtain a steady state of noise reduction under any conditions in the passenger compartment.

While the presently preferred embodiment of the present invention has been shown and described, it is to be understood that this disclosure is for the purpose of illustration and that various changes and modifications may be made without departing from the scope of the invention as set forth in the appended claims.

We claim:

1. A vehicle internal noise reduction system for reducing a noise sound within a passenger compartment by producing a canceling sound from a sound source based on a primary source signal having a high correlation with an engine vibration noise, the system comprising:

first canceling signal synthesizing means for synthesizing said primary source signal with a first filter coefficient of a first adaptive filter and for producing a canceling signal;

canceling sound generating means responsive to said canceling signal for generating a canceling sound from a sound source so as to cancel a noise sound within said passenger compartment;

error signal detecting means for detecting a state of noise reduction at a noise receiving point as an error signal;

compensation coefficients synthesizing means for synthesizing said primary source signal with a compensation coefficient and for outputting an output signal;

first filter correction amount calculating means responsive to said output signal from said compensation coefficients synthesizing means and to said error signal from said error signal detecting means for calculating a first correction amount and outputting a first correction amount signal;

first filter coefficients updating means for correcting said first filter coefficient to produce a corrected first filter coefficient based upon said first correction amount signal and for sending said corrected first filter coefficient to said first canceling signal synthesizing means;

second canceling signal synthesizing means for synthesizing said canceling signal with a second filter coefficient of a second adaptive filter and for outputting a synthesized canceling signal;

error signal adding means for adding said synthesized canceling signal and said error signal and for outputting a product of said addition as an addition signal;

second filter correction amount calculating means responsive to said canceling signal from said first canceling signal synthesizing means and said addition signal from said error signal adding means for calculating a second correction amount and outputting a second correction amount signal;

second filter coefficients updating means for correcting said second filter coefficient based upon said second correction amount signal and for producing a corrected second filter coefficient so as to cancel a deviation of a transmission characteristic between said canceling sound generating means and said error signal detecting means;

correction control means responsive to said addition signal, said error signal and said primary source signal for generating a correction control signal; and compensation coefficients correcting means responsive to said correction control signal for correcting a compensation coefficient from said second filter coefficients updating means and for sending said compensation coefficient representing an actual transmission characteristic between said canceling sound generating means and said error signal detecting means to said compensation coefficients synthesizing means.

2. The vehicle internal noise reduction system according to claim 1, wherein the system comprises a plurality of channels employing a Multiple Error Filtered X-LMS algorithm.

3. The vehicle internal noise reduction system according to claim 1, wherein said canceling sound generating means comprises at least one speaker.

4. The vehicle internal noise reduction system according to claim 1, wherein said error signal detecting means comprises at least one microphone.

5. The vehicle internal noise reduction system according to claim 1, wherein said primary source signal is an ignition timing signal.

6. The vehicle internal noise reduction system according to claim 1, wherein said primary source is a fuel injection pulse signal.

7. The vehicle internal noise reduction system according to claim 1, wherein said primary source signal inputted to said correction control means is displaced with a signal directly indicating an engine revolutionary speed.

8. The vehicle internal noise reduction system according to claim 1, wherein said correction control signal is generated when a change rate of the engine speed exceeds a specified value and further a difference of mean square values of said error signal and said addition signal exceeds a threshold value.

* * * * *